(12) United States Patent
Wong

(10) Patent No.: US 6,716,170 B2
(45) Date of Patent: Apr. 6, 2004

(54) BODY CHANNEL MOTION PICTURE PRODUCTION SYSTEM

(76) Inventor: Joseph Szeman Wong, 17C On Hong Bldg 15-23, Yinchong Street, Kowloon (HK)

( * ) Notice: Subject to any disclaimer, the term of this patent is extended or adjusted under 35 U.S.C. 154(b) by 0 days.

(21) Appl. No.: 10/186,272

(22) Filed: Jun. 28, 2002

(65) Prior Publication Data

US 2003/0225330 A1 Dec. 4, 2003

Related U.S. Application Data

(60) Provisional application No. 60/384,279, filed on May 30, 2002.

(51) Int. Cl.$^7$ ................................................ A61B 8/00
(52) U.S. Cl. ...................................... 600/443; 600/463
(58) Field of Search .............................. 600/407–471; 73/619–630; 128/916; 367/7, 11, 130, 138

(56) References Cited

U.S. PATENT DOCUMENTS

| | | | |
|---|---|---|---|
| 3,827,115 A | 8/1974 | Bom | |
| 4,327,738 A | 5/1982 | Green et al. | |
| 4,375,818 A | 3/1983 | Suwaki et al. | |
| 4,417,583 A | 11/1983 | Bechai et al. | |
| 4,802,487 A | 2/1989 | Martin et al. | 128/662.06 |
| 5,179,955 A | 1/1993 | Levene et al. | 128/662.02 |
| 5,247,939 A | 9/1993 | Silverstein et al. | 128/662.03 |
| 5,619,995 A | 4/1997 | Lobodzinski | 128/653.1 |
| 5,740,808 A | 4/1998 | Panescu et al. | 128/662.06 |
| 5,752,518 A | 5/1998 | McGee et al. | 128/662.06 |
| 5,848,969 A | 12/1998 | Panescu et al. | 600/462 |
| 5,899,861 A | 5/1999 | Friemel et al. | 600/443 |
| 5,931,788 A | 8/1999 | Keen et al. | 600/462 |
| 6,165,128 A | 12/2000 | Cespedes et al. | 600/463 |
| 6,406,431 B1 * | 6/2002 | Barnard et al. | 600/443 |

OTHER PUBLICATIONS

Takeda et al. A Novel Ultrasound Technique to Study the Biomechanics of the Human Esophagus in Vivo, Am J Physiol Gastrointest Liver Physiol, vol. 282, pp. G785–G793, 2002.

Norton et al. Initial Experience With a Steerable, Phased Vector Array Ultrasound Catheter in the GI Tract, Gastrointestinal Endoscopy, vol. 53, No. 4, pp. 496–499, Apr. 2001.

Menzel et al. Gastrointestinal Miniprobe Sonography: The Current Status, The American Journal of Gastroenterology, vol. 95, No. 3, pp. 605–615, Mar. 2000.

Taniguchi et al. Changes in Esophageal Wall Layers During Motility: Measurements With a New Miniature Ultrasound Suction Device, Gastronintestinal Endoscopy, vol. 39, No. 2, pp. 146–152, 1993.

Clenton Gastric Motility —The Role of Ultrasound, Radiography Today, vol. 56, No. 636, pp. 22–23, May 1990.

(List continued on next page.)

Primary Examiner—Ali Imam
(74) Attorney, Agent, or Firm—Bromberg & Sunstein LLP

(57) ABSTRACT

A system for producing a motion picture representing the movement of muscle lining a body channel includes a probe to be inserted in the channel, and a control unit to receive ultrasonic energy from the probe. More specifically, the probe has a transceiver capable of transmitting ultrasonic energy toward the muscle when within the body channel. The transmitted ultrasonic energy has a focal length to primarily focus on the muscle. The transmitted ultrasonic energy produces reflected ultrasonic energy (from the muscle) that the transceiver is capable of receiving. The control unit, which is in communication with the probe to receive the reflected ultrasonic energy, is capable of producing a motion picture signal representing the movement of the muscle. The motion picture signal is based on the reflected ultrasonic energy.

22 Claims, 5 Drawing Sheets

OTHER PUBLICATIONS

Rosch et al. A New Ultrasounic Probe for Endosonographic Imaging of the Uppper GI–Tract, Preliminary Observations, Endoscopy, vol. 22, No. 1, pp. 41–46, Jan. 1990.

Bertagnolli et al. Use of Endoscopic Ultrasound in Patients With Esophageal Motility Disorders, Gastroenterology Nursing, pp. 98–99, 1989.

Martin et al. A 20–MHZ Ultrasound System for Imaging the Intestinal Wall, Ultrasound in Medicine and Biology, vol. 15, No. 3, pp. 273–280, 1989.

Holt et al. Dynamic Imaging of the Stomach by Real–Time Ultrasound—A Method for the Study of Gastric Motility, Gut, vol. 21, pp. 597–601, 1980.

Kimmey Basic Principles and Fundamentals of Endoscopic Ultrasound Imaging, Endoscopic Untrasonography, pp. 4–13, Blackwell Science Publisher.

Zagzebski Physics and Instrumentation in Doppler and B–Mode Ultrasonography, Zwiebel: Introduction to Vascular Ultrasonography, Edition 4, pp. 17–43, W.B. Saunders Company, 2000.

Sivak, Jr. et al. High–Resolution Endoscopic Imaging of the GI Tract: A Comparative Study of Optical Coherence Tomography Versus High–Frequency Catheter Prober EUS, Gastrointestinal Endoscopy, vol. 54, No. 2, pp. 219–224, Aug. 2001.

Rosch et al. A New Ultrasonic Probe for Endosonographic Imaging of the Upper GI–Tract, Preliminary Observations, Endoscopy, vol. 22, pp. 41–46, Jan. 1990.

Bruce et al. Transvascular Imaging: Feasibility Study Using a Vector Phased Array Ultrasound Catheter, Echocardiography, vol. 16, No. 5, pp. 425–430, Jul. 1999.

* cited by examiner

US 6,716,170 B2

BODY CHANNEL MOTION PICTURE PRODUCTION SYSTEM

PRIORITY

This patent application claims priority from provisional U.S. patent application Ser. No. 60/384,279, filed May 30, 2002, entitled, "GI TRACT ULTRASOUND APPARATUS," and naming Joseph Szeman Wong as sole inventor, the disclosure of which is incorporated herein, in its entirety, by reference.

FIELD OF THE INVENTION

The invention generally relates to devices used to visualize internal body parts in medical applications and, more particularly, the invention relates to ultrasound devices used to visualize internal body parts in medical applications.

BACKGROUND OF THE INVENTION

A variety of different technologies have been developed over the years to give medical professionals a window into the human and animal bodies. Consequently, these technologies have become valuable tools to more effectively diagnose and treat disease. One such technology uses ultrasonic waves, which, in simplified terms, uses sound waves to gather information about internal body structures.

Ultrasonic devices currently are used in a wide variety of applications, ranging from visualization of a fetus to measuring the thickness of lesions and/or muscles lining the surface of the gastrointestinal tract ("GI tract"). When used within the GI tract, a probe typically is inserted through a person's esophagus and secured to the muscles lining the GI tract. From within the GI tract, the probe gathers information relating to lesion and/or muscle thickness, which is correlated by an external computer based system into a static graphical display.

Many GI tract disorders, however, are not caused by lesions. Instead, many such disorders are caused by improper movement of the muscles lining the GI tract (i.e., this type of disorder is a functional disorder). The art has responded to this problem by developing a number of techniques that indirectly measure GI tract muscle movement. More particularly, such current techniques measure some quality of the GI tract, and use the measured data to calculate information relating GI tract muscle movement. For example, one technique measures pH in the GI tract by inserting a long catheter through a person's nose to measure acidity changes over a 24 hour period. Another technique tests pressure within the GI tract by placing balloons at different locations within the GI tract. Both techniques collect data that is used to make an educated guess about the movement of muscles lining the GI tract.

Accordingly, as suggested above, current GI tract investigation techniques generally are uncomfortable to the patient because they require a rather invasive procedure for relatively long periods of time. In addition, long procedures increase diagnosis and treatment costs. Moreover, because current GI tract investigation techniques make indirect measurements, by their very nature they can produce erratic and inconclusive results.

SUMMARY OF THE INVENTION

In accordance with one aspect of the invention, a system for producing a motion picture representing the movement of muscle lining a body channel includes a probe to be inserted in the channel, and a control unit to receive ultrasonic energy from the probe. More specifically, the probe has a transceiver capable of transmitting ultrasonic energy toward the muscle when within the body channel. The transmitted ultrasonic energy has a focal zone to primarily focus on a pre-specified layer of the muscle. The transmitted ultrasonic energy produces reflected ultrasonic energy (from the muscle) that the transceiver is capable of receiving. The control unit, which is in communication with the probe to receive the reflected ultrasonic energy, is capable of producing a motion picture signal representing the movement of the muscle. The motion picture signal is based on the reflected ultrasonic energy.

In illustrative embodiments, the transceiver includes a portion capable of receiving the reflected energy, and a portion capable of transmitting the ultrasonic energy toward the muscle. The reflected energy includes low velocity and high velocity signals. The control unit thus includes a low pass filter for filtering out the high velocity signals. The low velocity signals are no greater than about ten centimeters per second.

The transceiver may transmit ultrasonic energy having frequencies of between about 12 and 30 megahertz. In some embodiments, the frequencies range from 15–20 megahertz. The probe further may include a medium container through which the ultrasonic energy is transmitted. In addition, at least a portion of the transmitted ultrasonic energy has a focal length that is no greater than about five centimeters. The control unit also may include an output for delivering the motion picture signals. In many embodiments, the channel includes one of the gastrointestinal tract and the genitourinary tract.

In accordance with another aspect of the invention, an apparatus produces a motion picture signal representing the movement of muscle lining a body channel. The body channel has a probe inserted therein to capture images of the movement. The apparatus thus includes a signal generator for producing an output signal that causes the probe to output an initial ultrasound signal with a given frequency. The given frequency provides a focal length for primarily focusing the initial ultrasonic signal on the muscle when the probe is within the body channel. The apparatus also includes an output operatively coupled with the signal generator. The output is capable of delivering the output signal to the probe. The focal length and transmitting frequency could be adjusted to optimize the image. In addition, the apparatus further includes a receiver capable of receiving a reflected ultrasonic signal from the probe, and a motion picture module operatively coupled with the receiver. The reflected ultrasonic signal is produced by the initial ultrasonic signal reflecting from the muscle. The motion picture module is capable of producing the motion picture signal representing the movement of the muscle. The motion picture is produced based on the reflected ultrasonic signal.

In some embodiments, the apparatus also includes an amplifier operatively coupled to the receiver, where the amplifier is capable of amplifying the reflected ultrasonic signal. The apparatus further may include a motion picture port operatively coupled with the motion picture module. The motion picture port is capable of transmitting the motion picture signal. The motion picture can be frozen and saved as a snapshot. The vector velocity of a layer of interest could be color coded and displayed.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

The foregoing and advantages of the invention will be appreciated more fully from the following further description thereof with reference to the accompanying drawings wherein.

DESCRIPTION OF ILLUSTRATIVE EMBODIMENTS

In illustrative embodiments of the invention, an imaging system displays the movement of muscle lining a body channel. Consequently, by using this system, medical professionals should be able to more efficiently diagnose and treat ailments to body channels within both people and animals. Details of various embodiments are discussed below.

Figure 1:
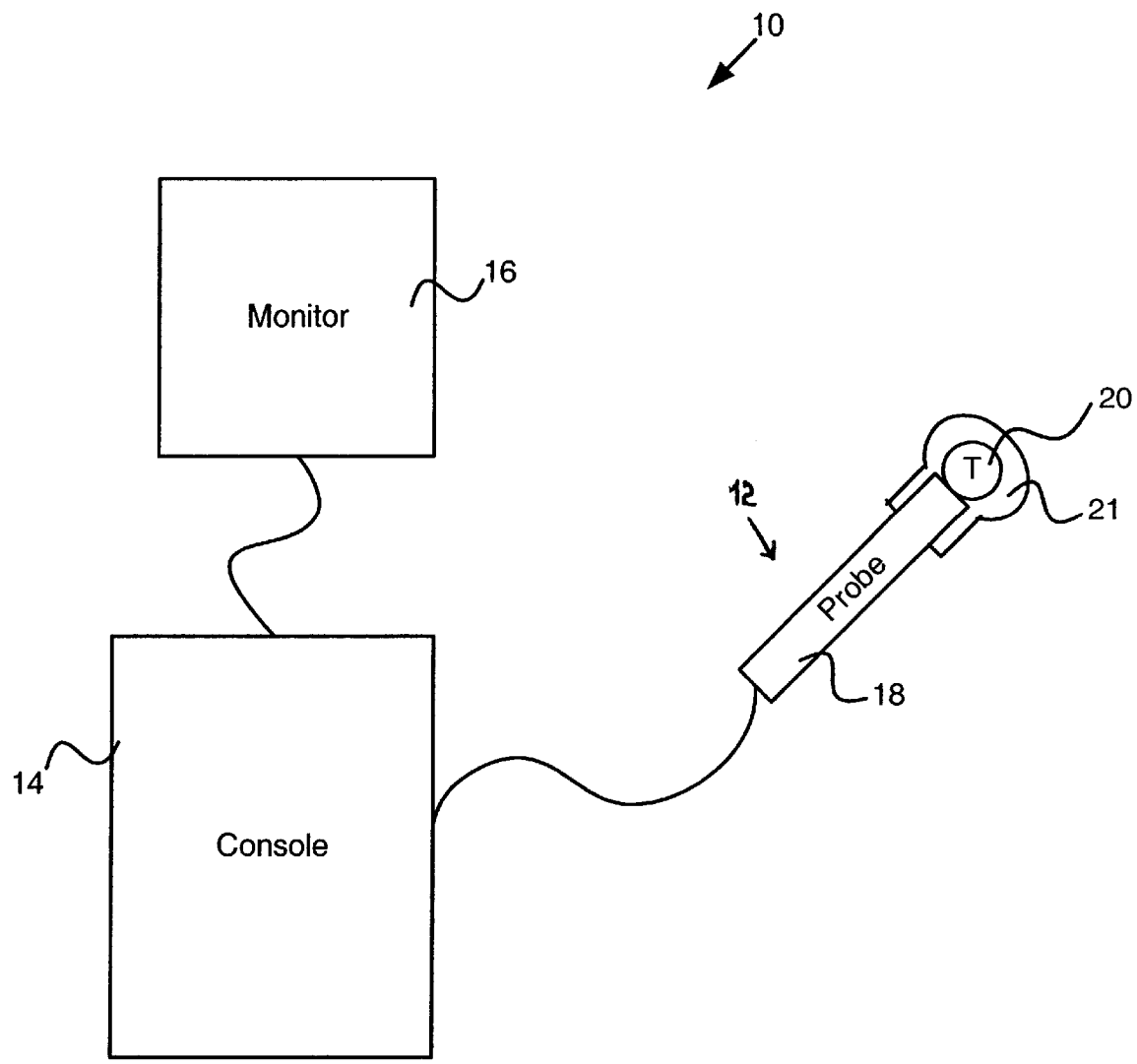
FIG. 1 schematically shows an ultrasound system that may be configured in accordance with illustrative embodiments of the invention.

FIG. 1 schematically shows an ultrasound system (hereinafter "system 10") configured in accordance with illustrative embodiments of the invention. The system 10 includes a probe 12 to both generate and gather the raw image data from within the body channel, a console 14 to process the raw image data received from the probe 12, and a monitor 16 to display a motion picture showing muscle movement within the body channel. It should be noted that the term "motion picture" is not intended to be limited to specific types of imaging media. Instead, any image that is moving, whether it is video, film, or other type of medium, may be used.

More specifically, in illustrative embodiments, the system 10 is an ultrasound-based system that transmits and processes ultrasound signals. As discussed below, the probe 12 transmits ultrasonic signals (within the body channel) that each has a focal length sized to primarily focus on the muscle lining such channel. As known by those skilled in the art, such ultrasonic signals are reflected from the muscles to produce reflected signals. These reflected signals have information representing the movement of the muscles. The probe 12 receives and forwards the reflected signals to the console 14 for processing. The console 14 uses the reflected signals to produce a motion picture signal, which then is forwarded to the monitor 16 for display.

The monitor 16 may be any conventional display device. Among other types, the monitor 16 may be a liquid crystal display flat screen display device, or a cathode ray tube display device. In some embodiments, the monitor 16 is coupled with the console 14 via a network connection. For example, the monitor 16 may be in communication with the console 14 via an Internet connection.

In a manner similar to the monitor 16, the probe 12 also may be any conventional probe used for such purposes. Exemplary types of probes include phased array probes and curvilinear probes. Of course, other types of probes may be used. Discussion of specific types of probes (as well as specific types of monitors) thus are exemplary and not intended to limit the scope of the invention.

The probe 12 thus may include a steerable and flexible shaft 18 with a transceiver 20 at its distal end. The transceiver 20 includes an array of crystals ("crystal array 22," see FIG. 3) that both transmit ultrasonic energy and receive the noted reflected ultrasonic energy. In some embodiments, the probe includes separate portions for transmitting and receiving ultrasonic signals. The probe 12 may be a rotating probe (i.e., configured to process data for the entire 360 degrees of the interior wall), or a linear probe (i.e., configured to process data for a portion of the wall, such as 120 degrees, or a longitudinal length of the wall). Moreover, the probe 12 illustratively is sized to have cross-sectional and length dimensions that are satisfactory for the intended purposes. For example, the probe 12 may have a length of about two meters and a cross-sectional diameter of about one centimeter. In other embodiments, an independent probe could be inserted into the body channel after appropriate lubrication. In still other embodiments, the probe 12 can be a catheter probe sized to pass through the accessory channel of an endoscope.

There are times when the sound transmission medium within the body channel is not conducive to transmitting ultrasonic signals. Accordingly, the probe 12 may include a medium container 21 secured about the transceiver 20 at the distal end of the probe 12. In illustrative embodiments, the container 21 is an expandable, medical grade latex balloon with a small lumen connected to its outside so that an ultrasound transmitting medium can be instilled. The volume of the transmitting medium is adjusted so that the balloon has adequate contact with the body channel wall without too much pressure exerted into the lumen. When inserted within the body channel, fluid (e.g., water or saline—as an ultrasound medium) may be directed along a connecting channel in the probe 12 to the balloon. The balloon fills until it contacts the muscle lined wall of the body cavity. When filled, the fluid should act as a sufficient medium to permit adequate signal transmission.

Many currently available probes can be repeatedly used in this application. It is recommended, however, that to ensure its sterility and integrity, probes should not be used more than a relatively low number of times (e.g., six times). Accordingly, in some embodiments, the probe 12 includes logic for counting the total number of times the probe 12 has been used. For example, the logic may include a chip (e.g., an application specific integrated circuit) that detects a new use, and accordingly increments an internal counter each time. After the counter reaches a preset maximum number, the chip may generate some indicia (e.g., a beeping sound) indicating that the maximum number of uses has been reached. Alternatively, the chip may disable the probe 12, such as by blocking the connection between the probe 12 and the console 14.

Figure 3:
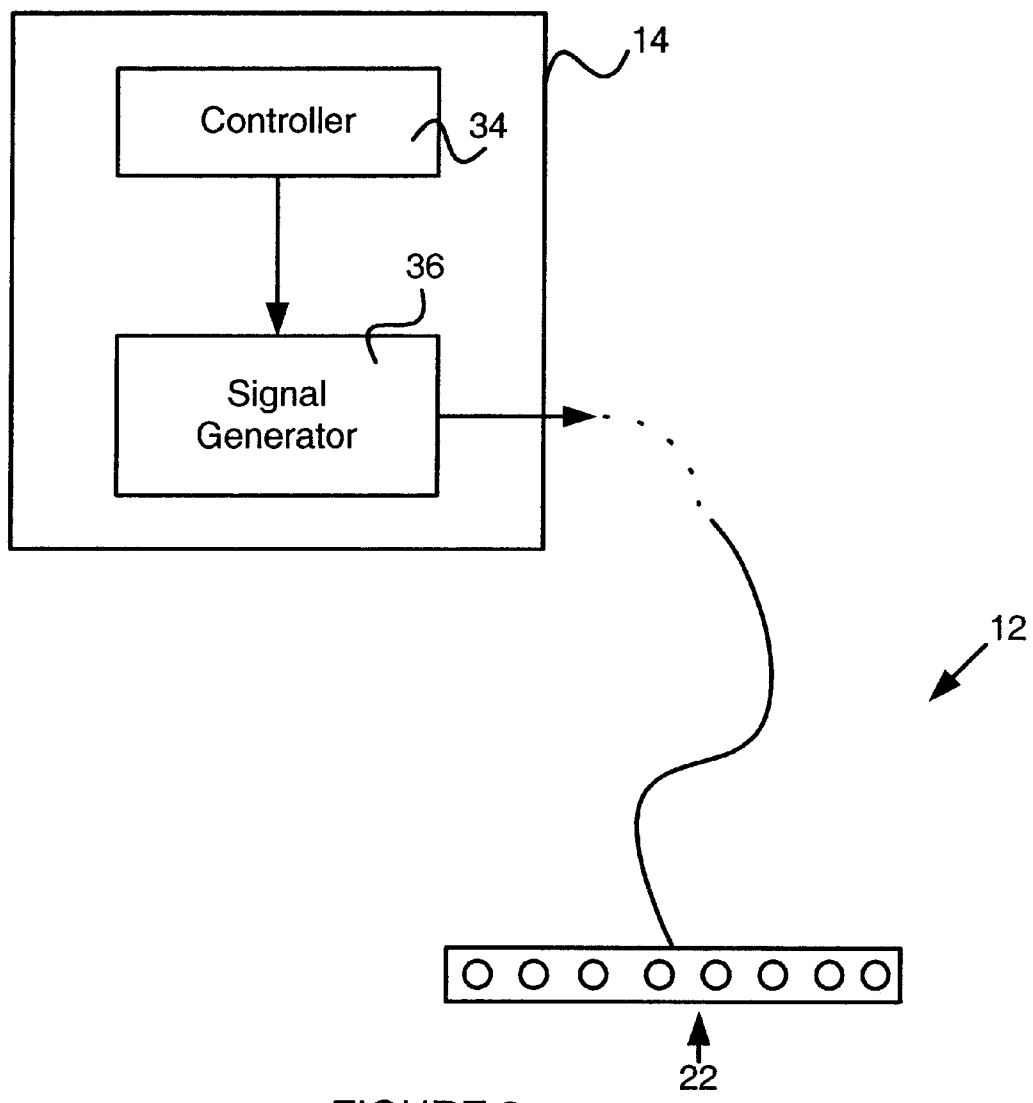
FIG. 3 schematically shows a transmit portion of the system shown in FIG. 1.

The console 14 includes logic for causing the probe 12 to transmit initial ultrasonic signals (hereinafter "initial signals") having the above noted focal lengths—i.e., a focal length that generates a focal zone to primarily focus the initial signal on a pre-specified layer of the muscle lining the body channel. In illustrative embodiments, this pre-specified layer is the outside layer of the muscle lining the body channel. This part of the console 14, which is referred to herein as the "transmit portion 24," is shown in FIG. 3 and described in greater detail below.

Figure 4:
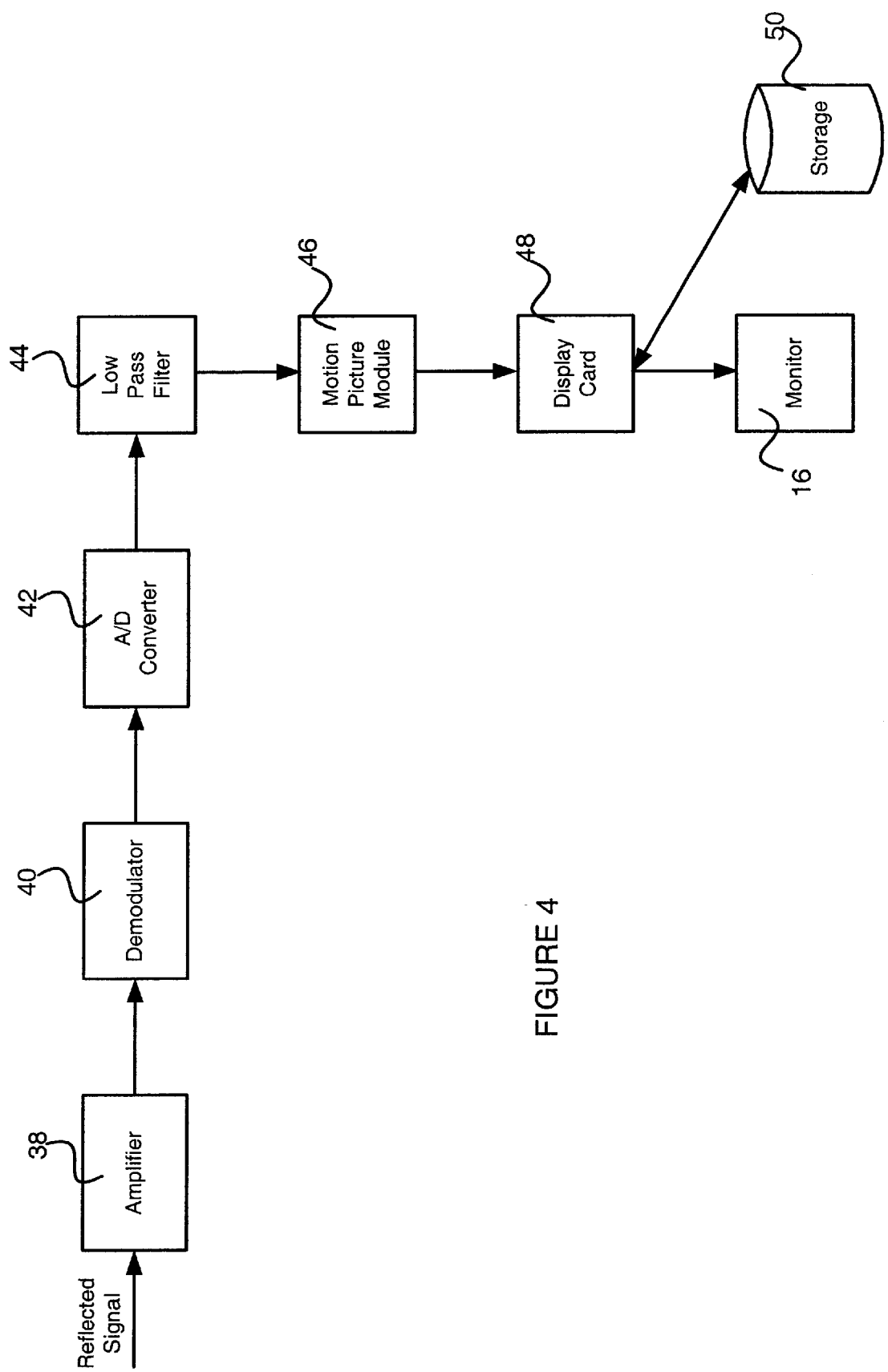
FIG. 4 schematically shows a receive portion of the system shown in FIG. 1.

The console 14 also includes logic for receiving and processing the reflected ultrasonic signals (hereinafter "reflected signals"). More specifically, this part of the console 14 (referred to herein as the "receive portion 26") includes logic for 1) processing the reflected signals, and 2) generating a motion picture signal capable of showing muscle movement based upon data parsed from the reflected signal. The receive portion 26 of the console 14 is shown in FIG. 4, which is described in greater detail below.

In addition to the transmit and receive portions 24 and 26, the console 14 may have additional logic and controlling devices commonly included in imaging devices. For example, the console 14 may include a control panel (not shown) to control console performance (e.g., to set the initial signal frequency), and volatile and non-volatile storage devices (schematically shown in FIG. 4 as reference number 50) to store motion picture data. By way of example, the storage devices 50 may store a motion picture of a healthy body channel. The monitor 16 then may display the healthy body channel in a split screen format with the body channel being investigated, thus assisting in the diagnosis and treatment processes.

In addition, the console 14 also may have a graphical user interface ("GUI") so that a user can adjust parameters that control the behavior of the probe. The GUI also can enable the probe to switch between different modes. The GUI can permit a motion picture produced to be displayed in real time, add a color coded hue to the moving muscle, or other functionality. A control button in the GUI can be activated so that a still picture may be obtained and stored at any time. It further can include functionality to perform calculations and measurements on muscle layers.

To improve its overall functionality, the console 14 also may include networking logic (not shown) to couple with a network (e.g., a local area network, wide area network, and/or the Internet). Among other benefits, networking logic may be useful by permitting an image to be transmitted to a remote location for analysis. In addition, the console 14 also may include a wireless transceiver (not shown) to operate wireless devices.

Figure 2:
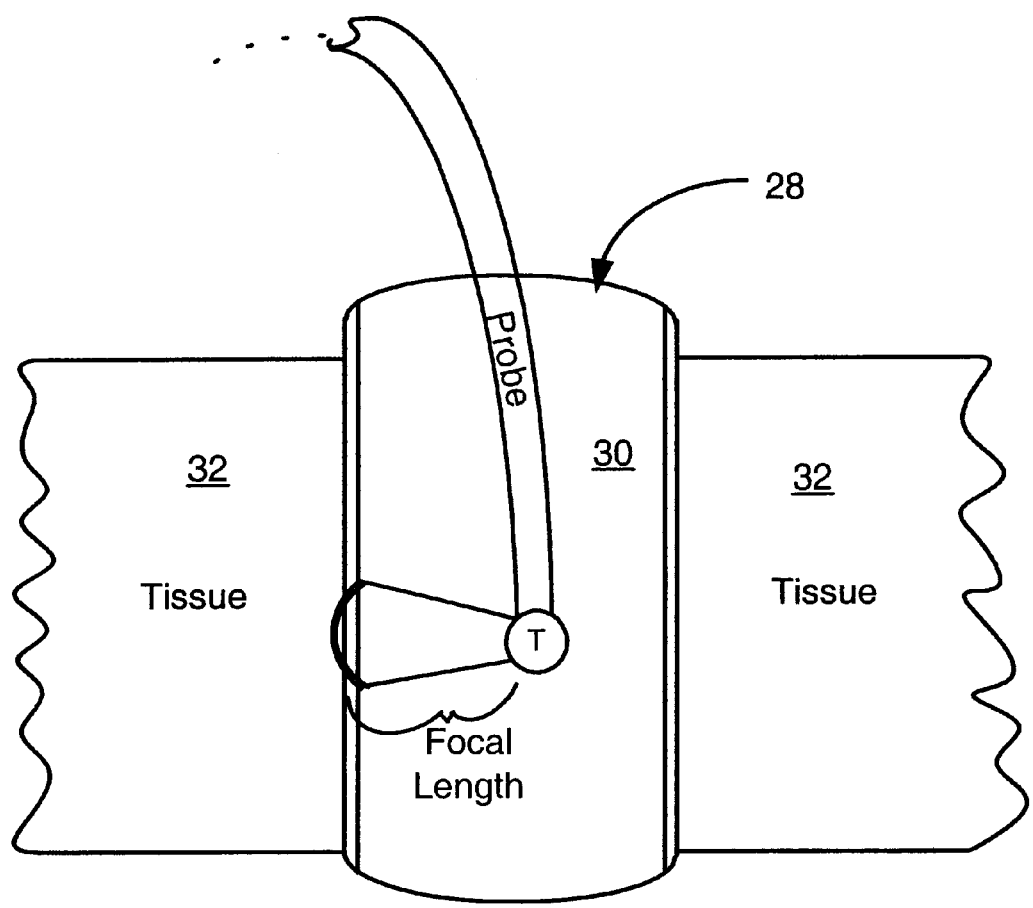
FIG. 2 schematically shows a cross-sectional view of the system shown in FIG. 1 being used in a muscle lined body channel.

FIG. 2 schematically shows the probe 12 when inserted within an exemplary body channel 28. An endoscope or other similar device may be used to facilitate probe insertion. The probe 12 preferably is inserted within the channel 28 so that the transceiver 20 does not contact the interior walls 30 when in use. In illustrative embodiments, the body channel 28 may be the gastrointestinal tract (referred to herein as the "GI tract") or the genitourinary tract (referred to herein as the "GU tract"). Accordingly, when used in the GI tract, for example, the system 10 displays movement of the surface muscles to determine if motility is within acceptable levels.

As suggested above, the depth of penetration of the initial signal is selected so that it focuses primarily on the interior walls 30, which are lined with the muscle to be viewed. Consequently, the initial signal should not transmit significant amounts of energy toward tissue 32 that is external to the channel 28. Reflected signals from such tissue 32 thus should be relatively weak and intentionally discarded. By way of example, when used within the GI tract, focal lengths focus primarily on the muscle lining the GI tract. The strength of reflected ultrasonic energy from other tissue 32 or organs external to the channel 28 (e.g., the heart) thus is not the focus of interest. Moreover, as discussed below in greater detail, the receive portion 26 of the console 14 filters out signals reflected from high velocity tissue, such as the heart.

Exemplary focal lengths within the GI tract should be no greater than about five centimeters (e.g., about two to four centimeters). To produce this focal length, the transmit portion 24 of the console 14 sets the initial signal to a specific frequency. Frequencies between about 12 and 30 megahertz should provide satisfactory results. In illustrative embodiments, the frequency is set to between about 15 and 20 megahertz.

The size of the transceiver 20 also has an effect on focal zone. In particular, the radius of curvature of the transceiver 20 should be large enough to provide such focal zones. More specifically, when used with the noted frequencies, the crystal array 22 in the transceiver 20 should have its crystals arranged so that they collectively are aligned in a relatively straight manner. The focal zone thus is a function of both the initial signal frequency and the curvature of the crystal array 22 in the transceiver 20. Accordingly, if one such parameter is changed, the other should be changed to ensure an appropriately sized focal zone.

FIG. 3 schematically shows the transmit portion 24 of the console 14, which, in concert with the probe 12, generates the above discussed initial signal. More specifically, the transmit portion 24 includes a controller 34 having programming logic for setting a signal frequency, and a signal generator 36 (e.g., a modulator) that generates an electrical output signal based upon frequency information received from the controller 34. When in use, the signal generator 36 transmits the electrical output signal to the probe 12, which causes the crystals in the probe 12 to generate and transmit the noted initial signal (i.e., an ultrasonic signal) at the frequency specified by the controller 34. As noted above, the frequency is selected to ensure that 1) the focal length is appropriately sized for the body channel being investigated, and 2) the resolution is satisfactorily obtained for such body channel.

FIG. 4 schematically shows the receive portion 26 configured in accordance with illustrative embodiments of the invention. As noted above, the receive portion 26 processes the reflected signals for display as a motion picture on the monitor 16 shown in both FIGS. 1 and 4. Accordingly, there is a closely controlled time synchronization between the transmitted and received ultrasound wave packets, as well as the size of the packets. In this way, a color coded velocity signal can be superimposed to what appears to be a B-mode picture. The receive portion 26 includes an amplifier 38 to amplify the reflected signal, a demodulator 40 to demodulate the reflected signals (thus permitting the information of interest to be retrieved), and an analog-to-digital converter 42 for converting the demodulated analog signal into a digital signal. The amplifier 38, demodulator 40, and analog-to-digital converter 42 may be conventionally available components.

In accordance with illustrative embodiments of the invention, the receive portion 26 also includes a low pass filter 44 for removing high frequency shift components from the return signal (i.e., it removes signals undesirably received from high velocity tissue). For example, the heart typically moves at a velocity of about 20 centimeters per second, while the muscle lining the GI tract typically moves at velocities of about 2 centimeters per second. Accordingly, signals reflected from the heart have a high frequency and thus, are removed by the noted low pass filter 44. This is a desired outcome because, as noted above, such high frequency portions of the reflected signals are considered to be noise. Conversely, as noted above, signals reflected from muscle lining the GI tract have a low frequency and thus, pass through the noted low pass filter 44. The maximum frequencies permitted to pass through the low pass filter 44 thus are selected based upon the range of frequencies expected to be produced by ultrasonic energy reflecting from the muscles of interest. Accordingly, in a manner similar to the prior noted receive portion 26 elements, the low pass filter 44 may be any conventional low pass filter capable of performing the noted functions.

The receive portion 26 also includes a number of elements that generate the actual motion picture signal. To that end, the receive portion 26 also includes a motion picture module 46 for generating the motion picture signal from data within the digital signal passed through the low pass filter 44, and a display card 48 displaying the motion picture signal on the monitor 16. The monitor 16 and storage device 50 are also shown in FIG. 4 simply to demonstrate their communication with the receive portion 26.

Figure 5:
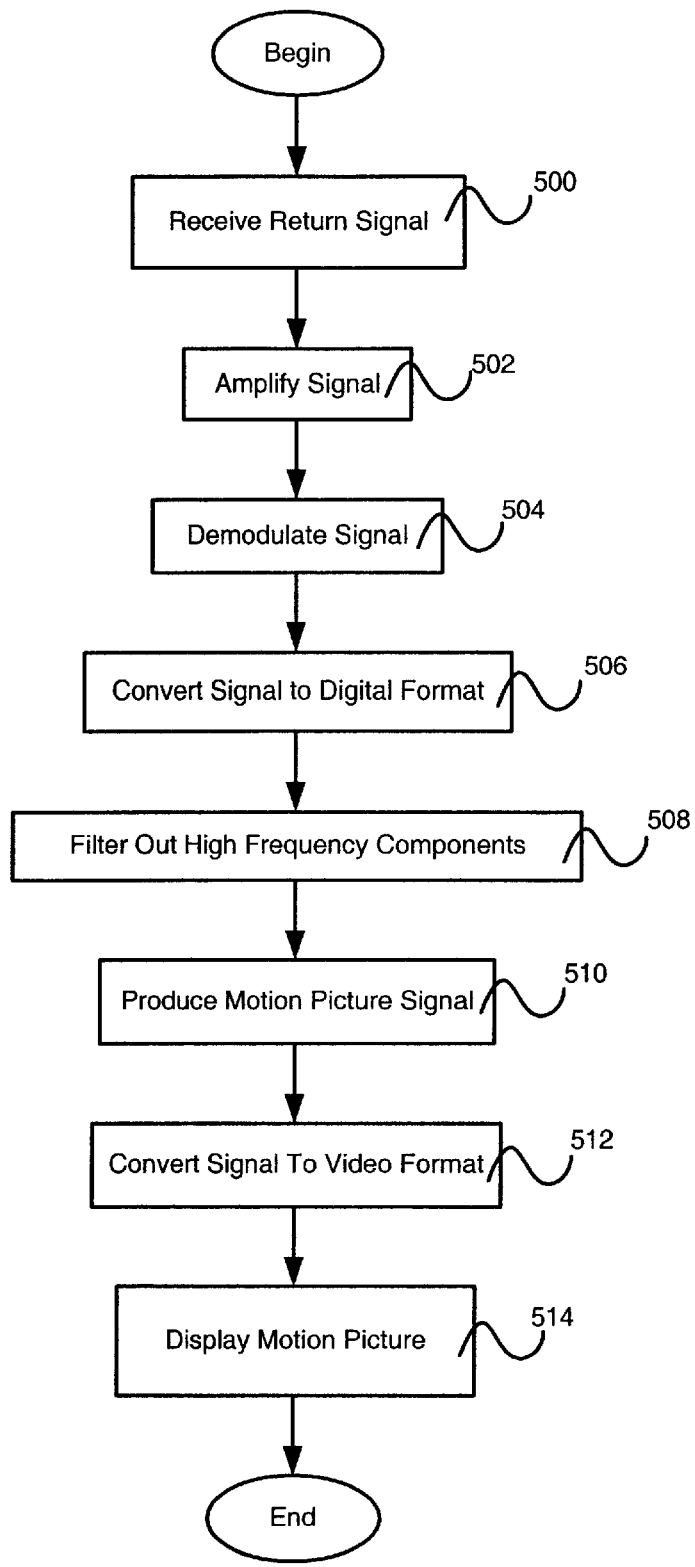
FIG. 5 shows an exemplary process used by illustrative embodiments to produce a motion picture of a body channel.

FIG. 5 shows an exemplary process executed by the receive portion 26 of the console 14 to produce the motion picture representing the moving muscle. The process begins at step 500, in which the receive portion 26 receives the reflected signals via the probe 12. The process then continues to step 502, in which the amplifier 38 amplifies the return signal. The demodulator 40 then demodulates the return signal to remove the information of interest from the return signal (step 504). Specifically, in accordance with conventional processes, the carrier signal carrying the information relating to muscle movement is removed, thus leaving the muscle movement information only.

The remaining information, which is in an analog form at this point in the process, then is converted to a digital signal by the analog-to-digital converter 42 (step 506). The resulting signal then is filtered by the (digital) low pass filter 44 (step 508), thus removing high velocity information. Accordingly, this step leaves the low velocity information intact for further processing. As noted above, the low velocity information includes the data relating to muscle movement within the body channel being investigated.

The motion picture module 46 then processes the digital low velocity information to produce a motion picture signal representing movement of the body channel muscle (step 510). The processed information from the reflected ultrasound signals are resolved as velocity information (coded as different color maps) superimposed on the muscle layers that are mapped to the position of a scanning beam. Thus, in some embodiments, the motion picture module 46 applies color codes to the motion picture signal to more easily display muscle movement. For example, as a muscle moves away from a viewing plane, the muscle may become blue. Conversely, as the muscle moves toward the same viewing plane, the muscle may become red.

This results in converting the low velocity digital data into a colored graphical representation. Conventional processes may be used to perform this, such as those used by currently available ultrasound devices. The motion picture module 34 also may execute other post-processing operations, such as sharpening the tissue borders and increasing or decreasing the log compression.

The process then continues to step 512, in which the motion picture signal is forwarded to the display card 48. As discussed above, the display card 48 converts the motion picture signal into a video signal for display by the monitor 16. The motion picture then may be displayed on the display device (step 514), thus completing the process.

It should be noted that some of the steps in the above noted process may be executed in a different order. For example, the filtering step (step 508) may be executed before the conversion step (step 506). Of course, in such case, the low pass filter 44 would be an analog filter. In a similar manner, additional steps known by those skilled in the art may be executed to generate the motion picture.

When in use, the probe 12 may be inserted into the channel in a conventional manner. For example, the probe 12 may be inserted into the GI tract via a lumen in an endoscope. Fluid may be instilled into the channel to facilitate signal transmission. After it is positioned, the probe 12 may begin transmitting and receiving ultrasonic signals. Retrieved motion pictures may be stored on the storage device 50 while simultaneously being displayed on the monitor 16. Motion pictures thus can be generated in real time as the muscle in the channel moves. Pharmacological agents may be administered as a stimulant, and muscle layer responses can be studied. In contrast to prior art techniques, it is anticipated that motion pictures having a relatively short duration (e.g., ten minutes) can be used to make a satisfactory assessment of the movement of the muscles being investigated. Moreover, this technique permits a direct examination of such muscles rather than the noted indirect prior art examination methods.

Some embodiments may apply to other forms of data transmission waves. For example, some embodiments may apply to non-sound wave based transmission waves. Other ultrasonic embodiments permit various modes of operation, such as the M-mode and B-mode. It also should be noted that ultrasound encompasses well known Doppler techniques.

Various embodiments of the invention may be implemented at least in part in any conventional computer programming language. For example, some embodiments may be implemented in a procedural programming language (e.g., "C") or an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and method may be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques).

The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made that will achieve some of the advantages of the invention without departing from the true scope of the invention. These and other obvious modifications are intended to be covered by the appended claims.

What is claimed is:

1. A system for producing a motion picture representing the movement of muscle lining a body channel, the system comprising:

a probe having a transceiver capable of transmitting ultrasonic energy toward the muscle when within the body channel, the transmitted ultrasonic energy having a focal zone to primarily focus on a pre-specified layer of the muscle, the transmitted ultrasonic energy producing reflected ultrasonic energy from the muscle, the transceiver being capable of receiving the reflected energy; and a control unit in communication with the probe to receive the reflected ultrasonic energy, the control unit being capable of producing a motion picture signal representing the movement of the muscle, the motion picture signal being based on the reflected ultrasonic energy.

2. The system as defined by claim 1 wherein the transceiver includes a portion capable of receiving the reflected energy, the transceiver also including a portion capable of transmitting the ultrasonic energy toward the muscle.

3. The system as defined by claim 1 wherein the reflected energy comprises low velocity and high velocity signals, further wherein the control unit includes a low pass filter for filtering out the high velocity signals, the low velocity signals being no greater than about two centimeters per second.

4. The system as defined by claim 1 wherein the transceiver transmits ultrasonic energy having frequencies of between about 12 and 20 megahertz.

5. The system as defined by claim 1 wherein the probe further includes a medium container through which the ultrasonic energy is transmitted.

6. The system as defined by claim 1 wherein at least a portion of the transmitted ultrasonic energy has a focal length of no greater than about two centimeters.

7. The system as defined by claim 1 wherein the control unit includes an output for delivering the motion picture signals.

8. The system as defined by claim 1 wherein the channel includes one of the gastrointestinal tract and the genitourinary tract.

9. An apparatus for producing a motion picture signal representing the movement of muscle lining a body channel, the body channel having a probe inserted therein to capture images of the movement, the apparatus comprising:

a signal generator for producing an output signal causing the probe to output an initial ultrasound signal with a given frequency, the given frequency providing a focal zone for primarily focusing the initial ultrasound signal on a pre-specified layer of the muscle when the probe is within the body channel;

an output operatively coupled with the signal generator, the output capable of delivering the output signal to the probe;

a receiver capable of receiving a reflected ultrasonic signal from the probe, the reflected ultrasonic signal being produced by the initial ultrasonic signal reflecting from the muscle; and a motion picture module operatively coupled with the receiver, the motion picture module capable of producing the motion picture signal representing the movement of the muscle, the motion picture being produced based on the reflected ultrasonic signal.

10. The apparatus as defined by claim 9 further including a low pass filter operatively coupled with the receiver, the low pass filter being capable of filtering out high velocity signals.

11. The apparatus as defined by claim 9 further including an amplifier operatively coupled to the receiver, the amplifier being capable of amplifying the reflected ultrasonic signal.

12. The apparatus as defined by claim 9 further comprising a motion picture port operatively coupled with the motion picture module, the motion picture port being capable of transmitting the motion picture signal.

13. The apparatus as defined by claim 9 further comprising a control unit that controls qualities of the output ultrasound energy.

14. The apparatus as defined by claim 9 wherein the given frequency is between about 12 and 30 megahertz.

15. The apparatus as defined by claim 9 wherein the channel is one of the gastrointestinal tract and the genitourinary tract.

16. A computer program product for use on a computer system for producing a motion picture signal representing the movement of muscle lining a body channel, the body channel having a probe inserted therein to capture images of the movement, the computer program product comprising a computer usable medium having computer readable program code thereon, the computer readable program code comprising:

program code for producing an output signal causing the probe to output an initial ultrasound signal with a given frequency, the given frequency providing a focal zone for primarily focusing the initial ultrasound signal on the muscle when the probe is within the body channel;

program code for delivering the output signal to the probe;

program code for receiving a reflected ultrasonic signal from the probe, the reflected ultrasonic signal being produced by the initial ultrasonic signal reflecting from the muscle; and program code for producing the motion picture signal representing the movement of the muscle, the motion picture being produced based on the reflected ultrasonic signal.

17. The computer program product as defined by claim 16 further including program code for filtering out high velocity signals.

18. The computer program product as defined by claim 16 further including program code for amplifying the reflected ultrasonic signal.

19. The computer program product as defined by claim 16 further comprising program code for transmitting the motion picture signal.

20. The computer program product as defined by claim 16 wherein at least a portion of the initial ultrasonic energy has a focal length of no greater than about five centimeters.

21. The computer program product as defined by claim 16 wherein the given frequency is between about 12 and 20 megahertz.

22. The computer program product as defined by claim 16 wherein the channel is one of the gastrointestinal tract and the genitourinary tract.

* * * * *